(12) United States Patent　　　　(10) Patent No.: US 12,605,549 B2
Sobrado Marinho et al.　　　　　　(45) Date of Patent: Apr. 21, 2026

(54) ELECTRONIC IMPLANT FOR NEUROMUSCULAR STIMULATION

(71) Applicants: UNIVERSIDADE DO PORTO, Oporto (PT); MECHANOBIONICS LDA, Oporto (PT)

(72) Inventors: Jorge Serafim Sobrado Marinho, Oporto (PT); José Alberto Peixoto Machado Da Silva, Oporto (PT); Joaquim Gabriel Magalhães Mendes, Oporto (PT)

(73) Assignees: UNIVERSIDADE DO PORTO, Oporto (PT); MECHANOBIONICS LDA, Oporto (PT)

( * ) Notice: Subject to any disclaimer, the term of this patent is extended or adjusted under 35 U.S.C. 154(b) by 347 days.

(21) Appl. No.: 18/255,709

(22) PCT Filed: Dec. 3, 2021

(86) PCT No.: PCT/IB2021/061311
§ 371 (c)(1),
(2) Date: Jun. 2, 2023

(87) PCT Pub. No.: WO2022/118278
PCT Pub. Date: Jun. 9, 2022

(65) Prior Publication Data
US 2023/0405328 A1　　Dec. 21, 2023

(30) Foreign Application Priority Data
Dec. 4, 2020　(PT) .......................................... 116919

(51) Int. Cl.
A61N 1/05　　(2006.01)
A61N 1/36　　(2006.01)
(Continued)

(52) U.S. Cl.
CPC ....... A61N 1/36139 (2013.01); A61N 1/0556 (2013.01); A61N 1/36125 (2013.01);
(Continued)

(58) Field of Classification Search
CPC .............. A61N 1/0556; A61N 1/36135; A61N 1/36067; A61N 1/36542; A61N 1/37211; A61N 1/37217
See application file for complete search history.

(56) References Cited

U.S. PATENT DOCUMENTS 5,358,514 A * 10/1994 Schulman .............. A61N 1/372
607/118
9,186,511 B2 11/2015 Bolea
(Continued)

FOREIGN PATENT DOCUMENTS

CA　　3098307 A1　10/2019
WO　2011079309 A2　6/2011

OTHER PUBLICATIONS

International Search Report and Written Opinion for Corresponding International Application No. PCT/IB2021/061311, 11 pages, Mar. 23, 2022.

*Primary Examiner* — Alyssa M Alter
(74) *Attorney, Agent, or Firm* — LUCAS & MERCANTI, LLP

(57) ABSTRACT

The present application describes an apparatus for Neuromuscular Stimulation constituted by an implantable medical device for in-situ neuromuscular electrical stimulation (INES) and a controlling external device. The medical device can be placed in the neighbourhood, implanted beneath or on the thickness of the knee tendons or ligaments.

17 Claims, 2 Drawing Sheets

(51) Int. Cl.
  *A61N 1/372* (2006.01)
  *A61N 1/378* (2006.01)

(52) U.S. Cl.
  CPC ..... *A61N 1/36146* (2013.01); *A61N 1/37223* (2013.01); *A61N 1/3727* (2013.01); *A61N 1/3787* (2013.01)

(56) References Cited

U.S. PATENT DOCUMENTS

| | | | |
|---|---|---|---|
| 9,687,376 B2 | 6/2017 | Liu | |
| 2013/0123568 A1 | 5/2013 | Hamilton et al. | |
| 2019/0321639 A1 | 10/2019 | Rao et al. | |

* cited by examiner

ELECTRONIC IMPLANT FOR NEUROMUSCULAR STIMULATION

CROSS-REFERENCE TO RELATED APPLICATIONS

This application is a 371 of PCT/IB2021/061311, filed Dec. 3, 2021, which claimed the priority of Portuguese Application No. 116919, filed Dec. 4, 2020, the contents of each of which are incorporated herein by reference.

TECHNICAL FIELD

The present application describes a Neuromuscular Stimulation apparatus constituted by an implantable medical device for in-situ neuromuscular electrical stimulation (INES) and a controlling external device.

BACKGROUND ART

Procedures for neuromuscular electrical stimulation (NMES) have received increased attention due to its capability to induce muscle activation and provide muscular strengthening to increase knee stability after the replacement of an injured ligament. From literature it is known that Neuromuscular Electrical Stimulation (NMES) applied to the quadriceps or hamstrings provides a faster recovery after an ACL/PCL repair. In-situ stimulation of the new ligament (graft) can further reduce the recovery time to 10 to 14 weeks and, to the best of our knowledge, the approach being proposed here has not been addressed before.

To the best of our knowledge, until present day, no specific devices have been proposed with the purpose of directly stimulating the reconstructed ligament and promote the reestablishment of proprioceptive communication after surgery.

U.S. Pat. No. 9,687,376 B2, Jun. 27, 2017, relates to an external continual electro-acupunctural stimulation approach and more specifically to knee braces having three stimulators for continual electro-acupunctural stimulation for in vivo and in situ therapeutic effects on analgesia and tissue regeneration and repair of the cartilage in the knee joint.

SUMMARY

The present application describes an apparatus for Neuromuscular Stimulation comprising an external unit comprising a control module and a transmitter resonant coil; and an implantable in-situ neuromuscular electrical stimulation device comprising a housing composed by a receiver resonant coil and an on-chip circuit; wherein the in-situ neuromuscular electrical stimulation device receives data and power from the external unit through an inductive link created between the receiver resonant coil and the transmitter resonant coil.

In a proposed embodiment, the on-chip circuit comprises a control unit module, a rectifier and regulator module, a power amplifier module, a demodulator and time synchronization module and a biphasic stimulator.

Yet in another embodiment, the implantable in-situ neuromuscular electrical stimulation device comprises a cuff electrode 1 and a cuff electrode 2.

Yet in another embodiment, the implantable in-situ neuromuscular electrical stimulation device further comprises a movement sensor 1 and a movement sensor 2.

Yet in another embodiment, the external unit further comprises a power supply module, a modulator module and a power amplifier module.

Yet in another possible embodiment, the inductive link comprises one of a simplex or half-duplex communication protocol under a modulation scheme that transmits a rectangular biphasic stimulating waveform programmed on the external controller with respect to its duration, phase, amplitude, frequency, and/or pulse width.

Yet in another embodiment, the control unit module comprises a digital stimuli waveform generator circuit adapted to produce signals that control the power amplifier module.

Yet in another embodiment, the stimuli waveform generator circuit produced signals that control the power amplifier module are adjusted in real-time accordingly with the input signals provided by movement sensor 1 and movement sensor 2.

Yet in another embodiment, the power amplifier module is adapted to generate a stimuli waveform with the appropriate power and duration established by the control unit.

Yet in another embodiment, the biphasic stimulator module is adapted to convert and alternate the phase of the stimuli waveform generated by the power amplifier module.

Yet in another embodiment, the stimuli waveform is transmitted through the cuff electrode 1 and cuff electrode 2 to deliver electrical stimuli waveform to tissue, tendons or ligaments of a user comprising the implantable in-situ neuromuscular electrical stimulation device installed under the skin.

Yet in another embodiment, the implantable in-situ neuromuscular electrical stimulation device installed under the skin of a user is positioned at least in one of the vastus medialis near the knee and/or over the proximal thigh over the vastus lateralis, and/or over near the femoral nerve proximally and/or vastus medialis, and/or over both the quadriceps and hamstrings simultaneously.

This application also describes a method for Biphasic Neuromuscular Stimulation resorting to the use of the Neuromuscular Stimulation Apparatus previously described, comprising the steps of:

define the stimulation parameters on an external unit that comprise at least one of a duration, phase, amplitude, frequency, and/or pulse width of the stimulation waveform;

transmit the stimulation parameters from the external unit to an implantable in-situ neuromuscular electrical stimulation device through an inductive link that comprises data and power that ensures the operation of said implantable stimulation device;

the implantable in-situ neuromuscular electrical stimulation device, being installed under the skin of the user, delivers electrical stimuli waveform to tissue, tendons or ligaments based on the stimulation parameters defined on the external unit to promote faster recovery, healing, rehabilitation and nerve regeneration restoring specific connections between sensory and motor axons.

GENERAL DESCRIPTION

The present application describes a stimulating apparatus constituted by an implantable device for in-situ neuromuscular electrical stimulation (INES) and an external device meant to provide power and control the operation of the implantable device.

Ligaments are short bands of tough, flexible tissue, made up of several individual fibers, whose main functions are to connect the bones of the body together and to provide a passive limit to the extension of the movement/rotation between bones.

The Anterior and Posterior Knee Cruciate Ligaments (ACL/PCL) constitute the connection structure that bonds the tibia and the femur. The ruptures of these ligaments, particularly the ACL, are among the most common ligament ruptures due to increased sports participation and population aging.

The ACL disruption is a major issue for athletes in a wide range of sports specially in soccer. Further to all the complications related with the breakdown of physical activity, the athletes must also face the instable and long program of rehabilitation before returning to sport activity, which however not always ensures achieving the same level of performance held before injury.

The common reconstruction of ACL/PCL injuries requires a surgery, where the debris are removed, and the ligaments are repaired using a self-graft procedure where in the majority of the cases, the injured ligament is completely teared off.

During the surgery, both ligament ends are reaped off and a new ligament is prepared using a ripped graft from the patient—usually a semitendinosus stripped from the sartorial fascia.

There are other tissue engineering techniques relying on scaffolds from biological materials, biodegradable polymers and composite materials.

Depending upon the ligament injury, full level of activity may not be possible before 3 to 4 months, and very severe ligament injuries can take up to 12 months or even longer. The required time to return to sports depends on extrinsic factors, such as the chosen graft and rehabilitation procedures. Even if knee stability is achieved to a good level, a knee extensor weakness ranging from 6% to 18% has been reported to occur still one to six years following reconstruction. A lower ability to contract the quadriceps muscles can be detected immediately after surgery, leading to muscle atrophy and decreased function. The key time milestone on knee rehabilitation is six months, and better recovery is attained on proprioception and functional capacity, only in full extension and complete flexion and no recovery on proprioception at middle extension.

This healing process typically requires a long time, before achieving complete healing. This fact is mainly due to the nature of the graft ligament and its hipovascularization; that causes a very slow and usually incomplete healing process.

When the ligament is rebuilt with the autograft technique, time is required for new natural bonding on tibia and femur bones to be formed. The graft ligament will naturally grow additional fibres as a response to increased exercise load and functional demands.

To speed up the healing process, Transcutaneous Neuromuscular Electrical Stimulation (NMES) has been combined with exercise to return full strength and motor capacity of the knee movements.

This NMES treatment is performed through the repeated application of current to depolarize motor nerves to restore and improve quadriceps function. The NMES treatment helps to restore quadriceps strength by facilitating recruitment of the muscle that may be inhibited by pain, effusion, or knee trauma.

The electrical stimulation electrodes can be placed over the vastus medialis near the knee and on the proximal thigh over the vastus lateralis, over near the femoral nerve proximally and vastus medialis, or even both the quadriceps and hamstrings simultaneously.

It is also recognized that the electrical stimulation applied to these injuries (or conceptually similar), accelerates nerve regeneration after injury and helps restoring specific connections between sensory and motor axons with the respective targets. The shorter the time of denervation and the fewer axons are misdirected in other (inappropriate targets), the better the recovery after denervation.

On the other hand, neuromuscular activity of immature nerve terminals during sprouting, increases the motor unit area and enhances the muscle strength.

The rehabilitation process generally focusses on biomechanical factors such as muscle strength, balance and plyometric function, giving lower importance to cognitive or neurological components. This lack of sensitivity, caused by the loss of signalling mechanoreceptors, alters the way how the associated brain neuroplasticity intervenes in controlling the knee movements. It is common knowledge that the rehabilitation programs emphasize the knee's movement, but this changes from a sensitivity guided movement, to a visual guided one, while the patient struggles to regain control of complex motor skills.

With the removal of the original ligament, also a neurological connection is lost. Although ligaments comprise mainly connective tissue, 1% of their area is made of mechanoreceptors. These mechanoreceptors are responsible for:

awareness of the position of the joint;

detection of movement;

efferent activity for recruitment and muscle contraction.

Scientific evidence proves that mechanoreceptors in the ACL provide a specialized sensory function that evaluates and regulates the quadriceps force. The strength deficits in the quadriceps after an ACL rupture and reconstruction may be a result to the loss of proprioceptive signals that report strain within harmless limits, even in the absence of any significant motor deficit.

The rapid recovery of muscle tone and tendon response to muscle contraction, particularly in the simultaneous recruitment of several muscles responsible for balance and lower limb gait, is a valuable help for speedy recovery of the patient who suffered rupture of the knee tendons or heel. Thigh muscle weakness often accompanies Anterior Cruciate Ligament (ACL) injury.

When comparing results of patients treated with ACL reconstruction, preserving and non-preserving the tibial remnants debris of the disrupted ACL, the first ones show better joint stability under dynamic conditions. So, there is a wide understanding that ACL works also as a sensory organ that can provide secondary stability from compensatory contracture muscles around the joint with a feedback system initiated by mechanoreceptors.

In fact, it is known that patients who had been subjected to ACL reconstruction, experiment difficulties on recovering the muscular recruitment related to the initial motion of the knee. This fact has personal, social, and economic consequences and even the complete regain of the function is never attained.

So far, all physiotherapy processes addressing the functional recovery of a member (upper or lower) affected by tendon rupture, rely on the external electrical stimulation ability to modulate contractile response during the recovery evolution of the patient.

As previously mentioned, an injury of the anterior cruciate ligament leads, (depending on the severity of the injury,) to a loss of the mechanoreceptors. Most of these receptors are present around insertion between the ligament and the tibia, the so called intermediate non articular intercondylar eminence. The ligament insertion on the inner wall of lateral condyle of the femur, confirms the importance of these nerve cells in proprioception, knee stability and movement. A decrease in the amount of these nerve cells compromises knee function. Nerve cells are not reproducible; therefore, it is not possible to regenerate a population of lost mechano-receptors.

However, a re-innervation process may occur. When nerve cells are lost, it is possible that the axons of cells close to the injured area prolong their axons to the critical area, re-innervating it. It means that, it is not possible to re-establish the sensitivity in the site where the mechanorecep-tors are lost, but it is possible that mechanoreceptors of the neighbouring areas, innervate the damaged area and send sensory information to the brain mimetizing as if they came from the area who lost nerve cells.

In the specific case of an ACL injury, surgery can be performed to insert the graft (mainly autograft or allograft) in an optimal and precise location. With this technique, the native tissue is induced to invade and grows inside the graft. This procedure is called "Remnant-Preservation ACL Reconstruction".

Because most mechanoreceptors are located in the sub-synovial layer near the tibial attachment of the ACL, it is possible that proprioceptive function is recovered by pre-serving the remnant of the tibial attachment of the ACL during ACL reconstruction. The axons of the mechanore-ceptors present in the sub-synovial layer should therefore grow to re-innervate the anterior cruciate ligament.

Throughout the years, remnant-preservation ACL recon-struction, has been showing positive results, with acceler-ated revascularization and re-innervation. The results are visible through histological observations on the amount of mechanoreceptor axons present in the lectured area, with improvements in the functionality of the knee. One of the factors that could promote muscle or ligament re-innervation is electrical stimulation.

So far, the principle of physiotherapy treatment and functional recovery of these patients is based on the belief that stimulating and strengthening the muscle or muscle groups that are connected to the affected tendon, can deliver a hypertrophy reaction response to the tendon and conse-quent its strengthening. This reasoning does not always correspond to what happens because the existence of post-operative fibrosis, frequently caused by inactivity or by inflammation, often prevents a beneficial impact of muscle contraction in strength, rigidity, and tensile strength.

Based on the above-mentioned facts, the present applica-tion describes the design and use of a microelectronic device comprising a microstimulator, two electrodes, and a move-ment sensor.

The two electrodes are intended to be placed in the ends of the reconstructed ACL, to facilitate the applied stimula-tion beneath the ligament nearby the tibial insertion and the remnants of the disrupted ligament. This localized and improved stimulation favours the growth of the remaining considerable number of mechanoreceptors, and their adhe-sion to the new ligament as well as its re-innervation.

On the other hand, since this stimulation is meant to be done synchronously with the movements of the leg and thigh, which are to be detected by the movement sensor, the proprioceptivity function of the knee joint is also re-trained and recovered. This shortens the recovery time needed for the patient to return to active life or sport.

This implantable device allows starting local stimulation from the very first moment of its installation, in the act of restorative and curative surgery liberating the patient from long dedicated time to carry out physiotherapy treatments, since the device will carry out a constant and programmed stimulation.

The movement sensor is meant to detect the on-set of muscles recruitment and activates the stimulation of the ligament, in order to promote the synchronized emission of sensory-evoked potentials to the cerebral cortex.

The developed device, and its use, represents a funda-mental improvement over traditional recovery methods for the rehabilitation and stimulation of muscle and severely injured joint tendons, beyond the knee joint.

BRIEF DESCRIPTION OF THE DRAWINGS

For better understanding of the present application, fig-ures representing preferred embodiments are herein attached which, however, are not intended to limit the technique disclosed herein.

DESCRIPTION OF EMBODIMENTS

Figure 1:
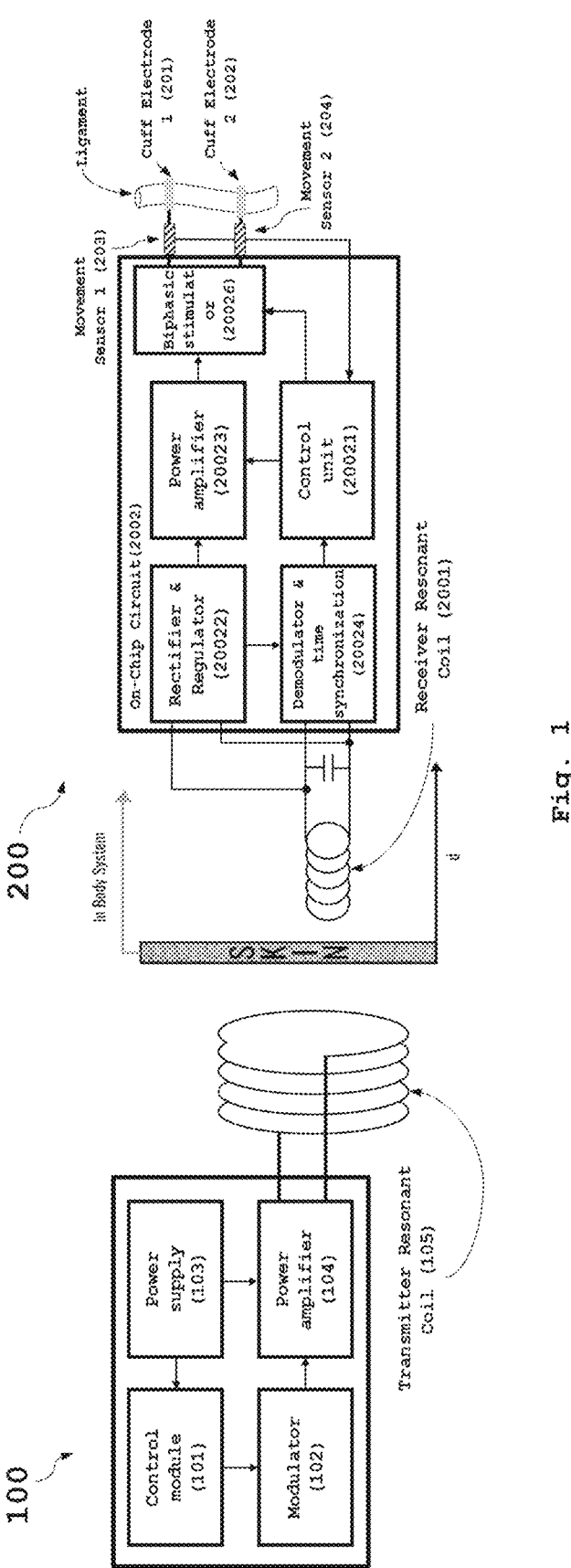
FIG. 1—Graphical illustration of the block diagram of the stimulation device, were the references are related with:
  100—external powering and control unit;
  101—control module;
  102—modulator module;
  103—power supply module;
  104—power amplifier module;
  105—transmitter resonant coil;
  200—in-situ neuromuscular electrical stimulation device;
  201—cuff electrode 1;
  202—cuff electrode 2;
  203—movement sensor 1
  204—movement sensor 2
  2001—receiver resonant coil;
  2002—on-chip circuit;
  20021—control unit module;
  20022—rectifier and regulator module;
  20023—power amplifier module;
  20024—demodulator and time synchronization module;
  20026—biphasic stimulator module.
Figure 2:
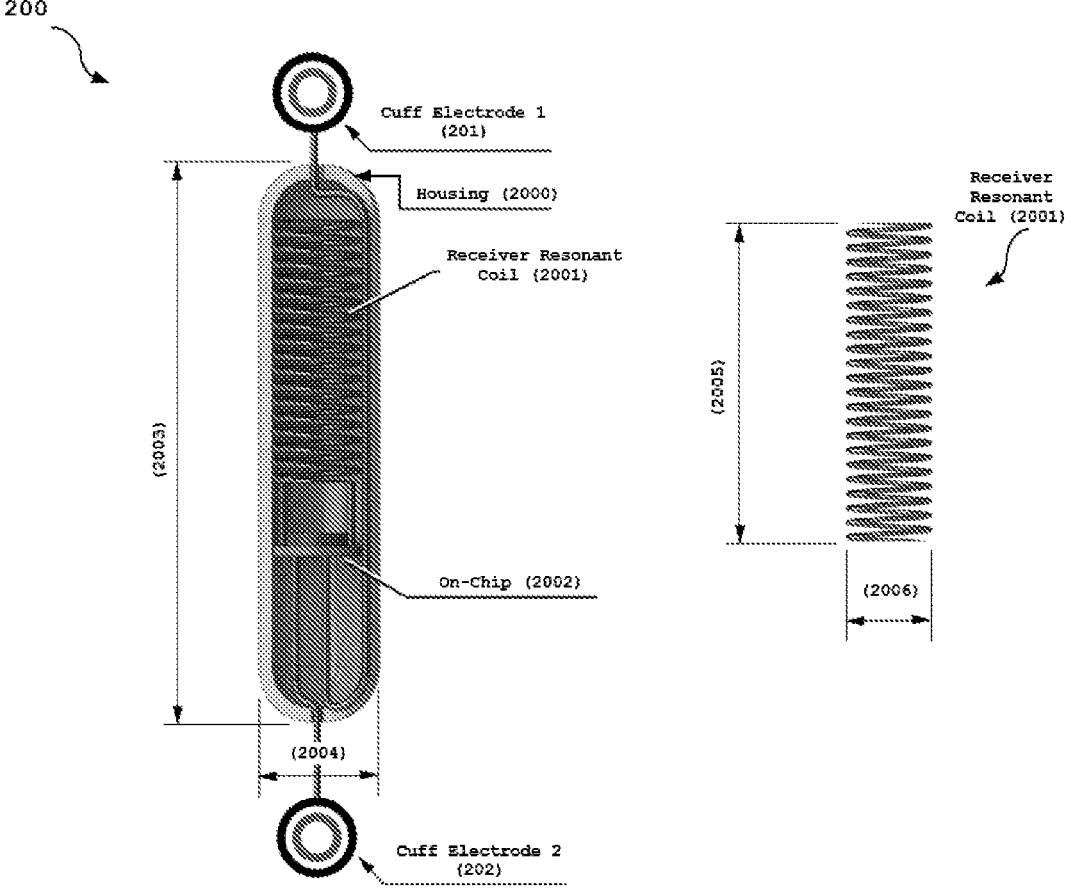
FIG. 2—graphical representation of the implantable in-situ neuromuscular electrical stimulation device and its coil, were the references are related with:
  200—in-situ neuromuscular electrical stimulation device;
  201—cuff electrode 1;
  202—cuff electrode 2;
  2000—device housing;
  2001—receiver resonant coil;
  2002—on-chip circuit;
  2003—overall length of the INES;
  2004—overall width of the INES;
  2005—overall length of the receiver resonant coil (2001);
  2006—overall width of the receiver resonant coil (2001).

With reference to the figures, some embodiments are now described in more detail, which are however not intended to limit the scope of the present application.

The external control device (100) of the proposed appa-ratus for Neuromuscular Stimulation, establishes an induc-tive link with the in-situ neuromuscular electrical stimula-tion (INES) device (200), which is implanted under the skin of the user, in one of the possible embodiments connected to knee ligaments through a pair of cuff electrodes (201, 202), in order to transmit data and power to said device (200). The goal of the proposed developed apparatus, in one of its possible solutions, is to strength the user's ligament, pro-moting a faster recovery and return to sports or active life.

The inductive link is used to power the INES implant (200), as well as to establish a either simplex or half-duplex communication between the external controller (100) and said implant (200), using a modulation scheme, e.g. a Binary Phase Shift-Keying modulation. The micro-stimulator (200) can be programmed for stimulus duration, amplitude, frequency, and pulse width of the rectangular symmetrical biphasic stimulating waveform.

The implantable INES device (200), for neuromuscular electrical stimulation of ligaments and muscular insertions, comprises a receiver resonant coil (2001) placed inside of the housing (2000) of the device (200), meant to capture the magnetic flux emitted by the transmitter resonant coil (105) of the external control unit (100). The housing (2000) also comprises a resonant capacitor, connected in parallel with the receiver coil (2001), an Application Specific Integrated Circuits (ASIC) that implements the harvesting of the power and the demodulation of the data transmitted by the external device (100), as well as the generation of a biphasic stimulation according to the parameters specified by the transmitted data. The ASIC, arranged inside of one on-chip circuit (2002) comprises an Rectifier and regulator module (20022) that establishes the ASIC power supply voltage; a Demodulator and Time Synchronization module (20024) that demodulates the received data and generates a clock time-base; a Control Unit module (20021) that generates a sequence of pulses with width, frequency and time positioning established by the demodulated data; a Power amplifier module (20023) to amplify the amplitude of the generated pulses; and a Biphasic Stimulator module (20026) that converts the sequence of pulses in the biphasic stimuli waveform to be applied to the tendon or ligament, delivering the electrical signal stimuli to the tissue via the cuff electrodes (201, 202).

The housing (2000) of the INES device (200) has a cylindrical shape with dimensions (2003, 2004) suitable for its insertion in the neighbourhood, beneath, or on the thickness of the knee tendons or ligaments. In one of the preferred embodiments, it is considered a maximum length of 10 mm (2003) and a maximum radius of 5 mm (2004). The housing of the device (200) incorporates a receiver resonant coil (2001), based on single layer short solenoid, with dimensions (2005, 2006) suitable for its placement inside of the housing (2000) and varying in order to fit the most appropriate carrier frequency of the communication link, that in one of the preferred embodiments it is considered to comprise a length of 6 mm (2005) and a 4 mm radius (2006).

The INES device (200) allows to produce flexible and precise biphasic current stimuli whose intensity, pulse width, frequency and on-off times are externally set by the external global controlling device (100).

On the receiver side (200), to recover the data and power signals transmitted by the external control device (100), a low-power RF front-end circuit is used which comprises a Rectifier and Regulator module (20022) that generates the voltages and currents appropriate for the ASIC operation, with low sensitivity to variations of the input voltage and load current, a Demodulator and Time Synchronization module (20024) that decodes the received data and generates the base clock signal that governs the overall timing of the ASIC, a Control Unit module (20021) that stores the received operation setting data and establishes the timing of the stimuli based on said setting data and the movement information provided by the movement sensors (2003, 204), a Power Amplifier (20023) that generates stimuli with the appropriate power/amplitude/frequency according the timing established by the control unit (20021), and the Biphasic Stimulator (20026) that alternates the phase of the stimuli generated by the Power Amplifier (20023).

All modules are designed in order to occupy a low silicon area and a low power consumption, making the ASIC suitable for bio-implantable devices.

The Rectifier and Regulator (20022) generates stable voltages to power supply the stimulator and the electronics, regardless of deviations of the input voltage or of the load current from 0 mA to maximum expected consumption current. Frequency compensation techniques are included to optimize transient response stability.

The Demodulator and Time Synchronization module (20024) detects the incoming modulated data signal captured by the internal resonant coil (2001), and translates the demodulated data and the recovered clock signal into a number of bits, or timed signals, that set the status of the control unit. This operation status is kept constant till new data is received.

The Demodulator and Time Synchronization module (20024) internally includes a Finite-State Machine that detects the header of the communication established between the external control unit (100) and the INES device (200) to receive the N-bit data with the stimulation parameters. After the header is detected, the next serial bits data are converted in parallel data and stored in an internal register. These bits set the operation parameters of the charge source and the signals that control the stimulation time pattern.

With regard to the Control Unit (20021) module, it comprises a digital stimuli generator circuit responsible for producing the signals that control the Power Amplifier (20023) and produce the desired stimulation pattern. The stimulation frequency can be programmed in a range of tens of Hz in preprogramed frequency steps. The pulse width and the duty-cycle of the stimulus signal can be programmed in the ranges of, respectively, a few hundreds of µs and from ⅛ to ¼. The digital stimuli generator operation is also controlled by the movement sensors (203, 204) so that the stimulation frequency and intensity are increased when a movement is detected, in order to promote the proprioceptive activity of the mechanoreceptors. The movement sensors (203, 204) are included in the conducting leads that connect the cuff electrodes (201, 202) to the microstimulator to avoid the inclusion of other devices in the system and duplicate the number of connections.

The Power Amplifier (20023) regulates the amount of charge, i.e. current intensity and duration, that characterizes the stimulation intensity/amplitude provided to the user by the cuff electrodes (201, 202). This intensity/amplitude is controlled by a charge source that comprises a 2-bit current mode Digital-to-Analog Converter (DAC) employing double-loop negative feedback which increases the output impedance of the current generator while maximizing the voltage compliance of the output transistor. The DAC creates a few hundred µA full-scale stimulation current that can be set in four equal size ranges.

In neuromuscular rehabilitation programmes, the stimulation parameters, especially the stimulation frequency and stimulus duty-cycle, may vary depending on the recovery phase of the patient. To deliver the electric impulses into the tissue, cuff electrodes (201, 202) in bipolar configuration were chosen because they can be placed around the user's ligament achieving better stimulation efficiency. In one of the proposed embodiments, electrodes made with a base of platinum-iridium alloy will be used due to the large reversible charge storage capacity of this material and thus to reduce the likeness of the onset of irreversible Faradaic reactions.

For the Biphasic Stimulator (20026), a H-bridge architecture is used in order to allow reversing the current in the load, said being achieved with an array of four transistors (two PMOS and two NMOS). This architecture has the advantage of requiring only one charge source and one power supply to ensure a perfectly charge-balanced biphasic waveform. A suitable power supply is used to accommodate the variable voltage drop in the tissue and electrode-tissue contact impedance load, referenced as several hundreds of ohms, as well as voltage drop in the switches of the array. Other switches may be used to passively shortening the tissue between pulses to remove any charge accumulated at the electrodes-tissue interfaces. Thus, a rectangular symmetrical biphasic waveform with constant interphase delay of tens of μs is produced. In the break periods, when no stimulation is applied, the two NMOS transistors remain on to passively shortening the tissue between pulses to remove any charge accumulated at the interface.

In a possible embodiment of present invention, the microstimulator (2002) can be programmed by a frame of N bits sent from the external controller (100) that controls the stimulation amplitude/intensity which is defined by a 4 bits array, stimulation frequency defined by a 2 bits array, pulse typically defined by 1 bit, and on/off stimulus times also defined by 1 bit. The data definition is transmitted only at the beginning of the connection between the external controller (100) and the microstimulator (2002). After the external controller (100) triggers the stimulation, it only sends only the carrier to power the implant (200) while stimulating the new ligament via electrodes (201, 202).

With regard to the Electrode-Tissue Interface, the internal modules of the on-chip circuit (2002) are responsible to ensuring the generation of the electrical pulses to be applied to the user's ligament via two cuff electrodes (201, 202), to induce muscle contraction/relaxation. The electrochemical reactions due to charge accumulations can be avoided, resorting to the use of correctly dimensioned electrodes (201,202), choosing the correct type of the material and configuration for the final application, and by using biphasic balanced stimulation instead of monophasic with an incorporated charge cancellation scheme. The bipolar configuration used on the cuff electrodes (201, 202) allows them to be placed around the ligament achieving a better stimulation efficiency, not affecting the functionality of the ligament. In a possible embodiment, Electrode cuffs made with a platinum-iridium alloy will be used due to the large reversible charge storage capacity of this material and thus to reduce the likeness of the onset of irreversible Faradaic reactions.

Together with the transmitter coil (105) and the control module (101), a power amplifier (104) typically of class-E type with semi-resonant primary is needed to amplify the power provided by the power supply (103) to generate higher currents in the coil (105) and thus higher magnetic flux to be captured by the implant (200). The external device (100) circuitry is designed using a step-by-step design procedure in order to optimize the driven inductive link to get a maximal link efficiency between coils (105, 2001). In this development, the size and shape of the coils, powering demands of the implant and coupling coefficient, set to 0.5 percent in worst case condition, were taken into account. The control and data signal modulated by the Modulator module (102), in one of the proposed embodiments, is set on a carrier frequency of 13.56 MHz. The modulator (102) also serves the dual purpose of providing power to the implant (200).

The invention claimed is:

1. An apparatus for Neuromuscular Stimulation comprising:
   an external unit (100) comprising a control module (101) and a transmitter resonant coil (105); and
   an implantable in-situ neuromuscular electrical stimulation device (200) comprising a housing (2000) composed by a receiver resonant coil (2001) and an on-chip circuit (2002);
wherein the in-situ neuromuscular electrical stimulation device (200) receives data and power from the external unit (100) through an inductive link created between the receiver resonant coil (2001) and the transmitter resonant coil (105), wherein the implantable in-situ neuromuscular electrical stimulation device (200) comprises a cuff electrode 1 (201) and a cuff electrode 2 (202), a movement sensor 1 (203) and a movement sensor 2 (204), wherein the movement sensor 1 (203) and the movement sensor 2 (204) are included in conducting leads connecting the cuff electrode 1 (201) and the cuff electrode 2 (202) to the on-chip circuit (2002), wherein the on-chip circuit (2002) comprises a control unit module (20021), a rectifier and regulator module (20022), a power amplifier module (20023), a demodulator and time synchronization module (20024) and a biphasic stimulator (20026), wherein the control unit module (20021) comprises a digital stimuli waveform generator circuit adapted to produce signals that control the power amplifier module (20023), the produced signals are adjusted in real-time accordingly with input signals provided by the movement sensor 1 (203) and the movement sensor 2 (204) to deliver a rectangular symmetrical biphasic stimulating waveform through the cuff electrode 1 (201) and the cuff electrode 2 (202).

2. The apparatus according to claim 1, wherein the external unit (100) further comprises a power supply module (103), a modulator module (102) and a power amplifier module (104).

3. The apparatus according to claim 1, wherein the inductive link comprises one of a simplex or half-duplex communication protocol under a modulation scheme that transmits a rectangular biphasic stimulating waveform programmed on the external controller (100) with respect to its duration, phase, amplitude, frequency, and/or pulse width.

4. The apparatus according to claim 1, wherein the power amplifier module (20023) is adapted to generate a stimuli waveform with the appropriate power and duration established by the control unit (20021).

5. The apparatus according to claim 1, wherein the biphasic stimulator module (20026) is adapted to convert and alternate the phase of the stimuli waveform generated by the power amplifier module (20023).

6. The apparatus according to claim 5, wherein the modulator module (102) sets a carrier frequency of 13.56 MHz and the power amplifier module (104) is of class-E type.

7. The apparatus according to claim 1, wherein the stimuli waveform is transmitted through the cuff electrode 1 (201) and cuff electrode 2 (202) to deliver electrical stimuli waveform to tissue, tendons or ligaments of a user comprising the implantable in-situ neuromuscular electrical stimulation device (200) installed under the skin.

8. The apparatus according to claim 1, wherein the implantable in-situ neuromuscular electrical stimulation device (200) installed under the skin of a user is positioned at least in one of the vastus medialis near the knee and/or over the proximal thigh over the vastus lateralis, and/or over near the femoral nerve proximally and/or vastus medialis, and/or over both the quadriceps and hamstrings simultaneously.

9. A method for Biphasic Neuromuscular Stimulation using the use of the Neuromuscular Stimulation Apparatus of claim 1, comprising:

defining a stimulation parameters on the external unit (100) that comprise at least one of a duration, phase, amplitude, frequency, and/or pulse width of the stimulation waveform;

transmitting the stimulation parameters from the external unit (100) to an implantable in-situ neuromuscular electrical stimulation device (200) through an inductive link that comprises data and power that ensures the operation of said implantable stimulation device (200); and delivering, through the implantable in-situ neuromuscular electrical stimulation device (200) installed under the skin of the user, a rectangular symmetrical biphasic stimulating waveform through the cuff electrode 1 (201) and the cuff electrode 2 (202) to tissue, tendons or ligaments based on the stimulation parameters defined on the external unit (100).

10. The apparatus according to claim 1, wherein the biphasic stimulator module (20026) uses a H-bridge architecture to allow reversing the current in the load to ensure a charge-balanced biphasic waveform with a constant interphase delay of tens of μs.

11. The apparatus according to claim 1, wherein the housing (2000) has a cylindrical shape with a maximum length of 10 mm (2003) and a maximum radius of 5 mm (2004).

12. The method according to claim 11, further comprising detecting movement by the movement sensor 1 (203) and the movement sensor 2 (204) included in conducting leads connecting the cuff electrode 1 (201) and the cuff electrode 2 (202) to the on-chip circuit (2002), and adjusting in real time the signals that control the power amplifier module (20023) accordingly with the input signals provided by the movement sensor 1 (203) and the movement sensor 2 (204).

13. The apparatus according to claim 1, wherein the receiver resonant coil (2001) has a length of 6 mm (2005) and a 4 mm radius (2006).

14. The apparatus according to claim 1, wherein the cuff electrodes (201, 202) are made with a base of platinum-iridium alloy.

15. The apparatus according to claim 1, wherein the cuff electrode 1 (201) and the cuff electrode 2 (202) are placed in the ends of the reconstructed anterior cruciate ligament (ACL), beneath the ligament nearby the tibial insertion.

16. The apparatus according to claim 1, wherein a stimulation frequency is programmable in a range of tens of Hz in preprogramed frequency steps, the pulse width is programmable in a range of a few hundreds of μs, and the duty-cycle is programmable from $\frac{1}{8}$ to $\frac{1}{4}$.

17. The apparatus according to claim 1, wherein the power amplifier module (20023) comprises a charge source that includes a 2-bit current mode Digital-to-Analog Converter employing double-loop negative feedback, the DAC creating a few hundred μA full-scale stimulation current set in four equal size ranges.

* * * * *